United States Patent [19]
Kobayashi et al.

[11] Patent Number: 5,897,868
[45] Date of Patent: Apr. 27, 1999

[54] SLURRY COMPOSITION FOR COSMETIC PRODUCT AND METHOD OF USE

[75] Inventors: Masaru Kobayashi, Woodstock; William Zavadoski, Madison, both of Conn.; Isao Imai, Saitama, Japan; Tohgo Murata, Chiba, Japan; Masaakira Horino, Kanagawa, Japan; Shigeru Kishida, Storrs, Conn.

[73] Assignee: U.S. Cosmetics Corporation, Dayville, Conn.

[21] Appl. No.: 08/658,461

[22] Filed: Jun. 5, 1996

[51] Int. Cl.$^6$ .............................. A61K 7/00; A61K 7/021
[52] U.S. Cl. .............................. 424/401; 424/69; 514/844
[58] Field of Search ...................... 424/69, 401; 514/844

[56] References Cited

U.S. PATENT DOCUMENTS

| | | | |
|---|---|---|---|
| 4,606,914 | 8/1986 | Miyoshi | 424/63 |
| 4,622,074 | 11/1986 | Miyoshi et al. | 106/308 |
| 4,648,908 | 3/1987 | Takasuka et al. | |
| 4,710,375 | 12/1987 | Takasuka et al. | 424/69 |
| 4,820,518 | 4/1989 | Murphy et al. | 424/401 |
| 4,837,011 | 6/1989 | Macchio et al. | 424/69 |
| 4,863,800 | 9/1989 | Miyoshi et al. | 428/403 |
| 4,988,502 | 1/1991 | Ounanian et al. | 424/63 |
| 4,992,262 | 2/1991 | Nakagaki et al. | 424/63 |
| 5,091,013 | 2/1992 | Miyoshi et al. | 106/505 |
| 5,310,578 | 5/1994 | Thurn-Muller et al. | 427/220 |
| 5,362,482 | 11/1994 | Yoneyama et al. | 424/69 |
| 5,486,233 | 1/1996 | Mitchell et al. | 106/416 |
| 5,578,311 | 11/1996 | Nagatani et al. | 424/401 |

FOREIGN PATENT DOCUMENTS

| | | |
|---|---|---|
| 81 079 615 | 6/1981 | Japan . |
| 58 072 512 | 4/1983 | Japan . |
| WO 94 15580 | 7/1994 | WIPO . |

OTHER PUBLICATIONS

Chemical Abstracts, vol. 95, No. 20, Nov. 16, 1981 (abstract of JP 81079615–above).
Chemical Abstracts, vol. 99, No. 8, Oct. 22, 1983 (abstracts of JP 5872512–above).

*Primary Examiner*—Robert H. Harrison
*Attorney, Agent, or Firm*—Graham & James LLP

[57] ABSTRACT

An aqueous slurry for cosmetic products, which comprises particles of pigments and/or extender pigments having a lipophilic moiety attached to the surface thereof and a cosmetically acceptable oily material dispersed in a liquid suspending medium consisting essentially of water.

9 Claims, No Drawings

SLURRY COMPOSITION FOR COSMETIC PRODUCT AND METHOD OF USE

BACKGROUND OF THE INVENTION

1. Field of the Invention

The present invention relates to a slurry for preparing cosmetic products and to such cosmetic products made through the use of this slurry. More specifically, the present invention provides a process for making smooth, adhesive, spreadable, long-lasting cosmetic products for external use, such as solid or solid-like, cake cosmetic products, such as make-up preparations.

2. Prior Art

Solid or solid-like, cake cosmetic products, such as make-up preparations (e.g. face powder, powder foundation, eye shadow, mascara, rouge and the like) are conventionally produced by filling a cosmetic powder into a metal or plastic pan or case followed by molding the powder by a press. In particular, the conventional manufacturing process for preparing cosmetic products includes mixing pigments and extender pigments and then atomizing them until the colors are well dispersed and uniform. Oily components and auxiliary agents, such as anti-bacterial agents, are added to the pigments and extender pigments and mixed and are atomized to disperse the oily components. The resulting mixture is then screened and further mixed until a uniform cosmetic powder is obtained. The cosmetic powder is filled into a pan or case and molded by a press.

This conventional process has several disadvantages:

i) Pigments and extender pigments have inherent strong hydrophilic properties; thereby, they will fade and/or discolor when contacted by perspiration, unless they are specially treated.

ii) The percentage of out-of-specification product is unacceptably high due to the non-uniformity of surface-color and/or surface-hardness of the molded cosmetic product.

iii) Multi-color molding and complex shape molding are quite expensive because of the cost of the shaping-mold, typically machined from metal.

iv) High labor costs are incurred, arising from the manual labor needed for adjustment and maintenance of equipment and the supply of bulk powder.

v) The loss of cosmetic powder during the molding process is significant.

vi) The work environment is undesirable due to the exposure of the workers to powdery dusty pigments and extender pigments.

It has previously been proposed to use pigments that have been made hydrophobic to solve the problem (i). For example, pigments or extender pigments and/or substrates that are surface-treated with silicone are strongly hydrophobic and can be used to prevent color fading and to improve the duration of use before reapplication. They can also be used for two-way cake (wet/dry application) cosmetics.

While the use of polysiloxanes ameliorates problem (i), the molding process becomes more complex and time consuming, and problems (ii), (iii), (iv), (v), and (vi) remain unsolved.

There have been some suggestions to solve problems (ii), (iii), (iv), (v), and (vi). For example, Japanese Patent 07-29904 and U.S. Pat. No. 4,967,810 suggest the use of a slurry in which pigments, extender pigments and/or substrates, and oily components are dispersed in an organic solvent for injection into the pan or case by an injection machine. These proposals may reduce the severity of problems (ii), (iii), (iv), and (v), but problem (vi) remains unsolved. Importantly, the use of organic solvents raises concerns about the possible dangers of flammability, environmental pollution, and harmful effects on the human body. Further, the choice of usable oily components is restricted depending on the kind or nature of the organic solvent used. For example, non-uniformity of the product is observed when an alcohol is used as the organic solvent with a silicone oil as the oily component of the cosmetic product.

SUMMARY OF THE INVENTION

It is an object of the present invention to provide an improved process of preparing cosmetic products.

More specifically, an object of the present invention is to provide a simplified process, thus decreasing the labor intensity of the conventional processes, to improve the work environment, and to provide a smooth, adhesive, spreadable, and long-lasting cosmetic product.

The present inventors discovered, during a study to solve previous problems, that when the pigments or extender pigments and/or substrates are made hydrophobic in an aqueous environment with an agent having a lipophilic moiety, such as water-insoluble metal salts of fatty acids, acylamino acids, hydrogenated lecithin, acyl collagen and the like, and rinsed and dried (but not completely dried), and then the oily components are added and the mixture thus formed is kneaded to form an aqueous slurry, the oily components are uniformly bound to the surface of the pigments and extender pigments and are not disassociated. Importantly, the slurry is obtainable without the need for organic solvents as all or part of the liquid medium in which the hydrophobic particles and the oily component are suspended.

The present invention thus provides an aqueous slurry for cosmetic products, which comprises particles of pigments and/or extender pigments having a lipophilic moiety attached to the surface thereof and a cosmetically acceptable oily material dispersed in a liquid suspending medium consisting essentially of water.

DETAILED DESCRIPTION OF THE INVENTION

In accordance with the present invention, pigments or extender pigments are made hydrophobic in an aqueous environment with an agent having a lipophilic moiety, such as a water-insoluble polyvalent metal salt of a fatty acid, an acylamino acid, hydrogenated lecithin, acyl collagen or like materials. In particular, the surface of the particles of the pigments and extender pigments carry lipophilic moieties (provided by the fatty acid etc.) linked to the surface of the particles by means of the polyvalent metal. Suitable polyvalent metals include alkaline earth metals, such as magnesium, and calcium, and other polyvalent metals, such as aluminum, titanium, zinc, zirconium and the like.

After rinsing and dehydrating the resultant hydrophobic pigment or extender pigment, but without completely drying, suitable oily components are added and the mixture is kneaded. Thereafter, water is added until the resultant slurry reaches an appropriate viscosity. This slurry is then used for the preparation of cosmetic products. The slurry composition may be injected into the back of a container for the cosmetic product by an injection machine, while the injected material is vacuum dehydrated via a filter on the top surface of the container. Then the cosmetic product is dried at an appropriate temperature.

The pigments or extender pigments that are made hydrophobic thus carry lipophilic groups on the surface thereof as a result of the treatment with the water-insoluble polyvalent metal salt of the fatty acid or other treating agent. The oily components will bind to the lipophilic-radicals on the pigments or extender pigments by displacing the water surrounding the treated pigments or extender pigments after the process of rinsing, dehydration, addition of the oily components, and kneading (mixing).

An aqueous slurry of the hydrophobic pigment and extender pigment and the oily component is thus formed without the use of an organic solvent. In particular, the pigments or extender pigments are coated with lipophilic-moieties and surrounding oily material, and are stable and form fine micelles and become an oil-in-water emulsion slurry without the use of a solvent or surfactant. The pigments and extender pigments are originally hydrophilic and do not require large energy to be dispersed in the water. After the surface treatment, the surface of each particle is coated with lipophilic-moieties and further covered by the surrounding oily component. Thus, the pigments and extender pigments will not agglomerate and will have excellent dispersibility for cosmetic use.

In a preferred embodiment of the invention, the aqueous slurry consists essentially of from about 50 to about 450%, by weight, of water and from about 1 to about 30%, by weight, of oily component, both based on the weight of the pigment and extender pigment particles.

Using the aqueous slurry of the invention including the hydrophobic pigments or extender pigments as described previously, cosmetic products with very intense color tone and without color bleeding can be produced. Moreover, the cosmetic products of the present invention do not exhibit color fading or color bleeding and have excellent skin "feel", adhesiveness, and smoothness compared to cosmetics that use pigments or extender pigments surface-treated in a conventional manner.

The agents useful for imparting hydrophobic properties to the pigments and extender pigments have a lipophilic moiety, and include water-insoluble polyvalent metal salts of fatty acids, acylamino acids, hydrogenated lecithin, acyl collagen and the like. Suitable polyvalent metals include the alkaline earth metals, such as magnesium or calcium, and other metals, such as aluminum, titanium, zinc or zirconium. Surface treatment agents having suitable lipophilic moieties are described in U.S. Pat. Nos. 4,606,914, 4,623,074 and 4,863,800 and Japanese Patents 60-69011 and 61-73775. The pigments and extender pigments may be made hydrophobic by mixing an aqueous solution of a water-soluble metal salt having a lipophilic moiety with the pigment and extender pigment particles, followed by addition of an aqueous solution of a water-soluble polyvalent metal salt, whereby the lipophilic moiety becomes linked to the particles by means of the polyvalent metal.

The amount of the surface-treating agent used in the present invention is dependent upon the particle size or specific surface area of the pigments or extender pigments being treated. Suitably, the amount of the surface-treating agent is from about 1 to about 20% by weight based on weight of the pigments or extender pigments, preferably from about 2 to about 5% by weight.

Suitable fatty acids providing the lipophilic moiety include lauric acid, myristic acid, palmitic acid, oleic acid, stearic acid, isostearic acid, behenic acid and the like. Water-soluble salts of such fatty acids may be formed with sodium or potassium.

Suitable acylamino acids include N-acyl-L-glutamic acid, N-acyl-N-methylglycine, N-acyl-N-methyl-β-alanine and the like. The acyl group may include a residue of lauric acid, myristic acid, palmitic acid, oleic acid, stearic acid, isostearic acid, and behenic acid. Water-soluble salts of such acylamino acids may be formed with sodium, potassium or ethanolamine.

Suitable hydrogenated lecithins include (1) hydrogenated natural lecithin obtained by extraction of lecithin from egg yolk, soy bean oil, corn oil, and rapeseed oil followed by hydrogenation; and (2) hydrogenated synthetic lecithin. The iodine value of the hydrogenated lecithin should preferably be less than 30. The term "lecithin" refers to the overall composition; therefore, the lecithin which can be used in the present invention does not have to be pure phosphatidyl choline, but may contain other phospholipids and neutral fats in addition to phosphatidyl choline. Water-soluble salts of the hydrogenated lecithins may be formed with sodium or potassium.

Suitable acyl collagens include those obtained by acylation of an oligopeptide or peptide. Useful oligopeptides or peptides are obtained by partially hydrolyzing protein and/or collagen and have n=1–100. The acyl group may include a residue of lauric acid, myristic acid, palmitic acid, oleic acid, stearic acid, isostearic acid, and behenic acid. Water-soluble salts of such acyl collagens may be formed with sodium or potassium.

The water-soluble salts having a lipophilic moiety used in the present invention are soluble at room temperature or in warm water. When one or more of these salts are added to the pigments and/or extender pigments the lipophilic moiety is adsorbed on the surface of the pigment and/or extender pigment particles. In order to complete the adsorption of the lipophilic moiety, an aqueous solution of a water soluble polyvalent metal salt, such as 1–30% by weight aqueous solution of a water-soluble salt of Al, Mg, Ca, Zn, Zr, or Ti is added in sufficient amount to give a proportion of 1–2 equivalents of the polyvalent metal salt of the fatty acid, acylamino acid, hydrogenated lecithin, or acyl collagen and the like. Useful water-soluble, polyvalent metal salts include aluminum sulfate, aluminum chloride, aluminum nitrate, aluminum potassium sulfate, magnesium sulfate, magnesium chloride, magnesium nitrate, magnesium potassium sulfate, calcium chloride, calcium nitrate, calcium acetate, zinc sulfate, zinc chloride, zinc nitrate, zinc acetate, zirconium sulfate, zirconium chloride, titanium oxysulfate, and titanium chloride. The polyvalent metal salt reacts with the salt of the fatty acid, acylamino acid, hydrogenated lecithin, acyl collagen and the like to form a water-insoluble reaction product which becomes chemically bound onto the surface of the pigment and extender pigment particles.

The oily component used in the present invention may be any cosmetically acceptable oily component commonly used in cosmetics, including hydrocarbon compounds, such as dimethicone, cyclomethicone, silicone oil, mineral oil, and squalane, and fatty acids, such as isostearic acid, myristic acid, stearic acid and esters thereof, glycerides, natural fats and oils, and the like. These oily component may be one oily material or a mixture thereof. The amount of the oily component useful in the present invention is dependent upon the size, specific surface area, or oil absorption of the pigments or extender pigments being treated. Suitably, the amount of the oily component is from about 1 to about 30% by weight of the pigments or extender pigments, preferably from about 2 to about 15%. by weight.

The pigments or extender pigments used in the present invention include organic and inorganic pigments, such as titanium dioxide, zinc oxide, zirconium dioxide, yellow iron oxides, black iron oxides, red iron oxides, ultramarine blues, Prussian blues, chromium oxides, chromic hydroxides, and the like, pearlescent pigments, such as mica coated with titanium dioxide, bismuth oxychloride, coal-tar pigments, natural pigments, silica beads, nylon beads, acrylic beads, talc, kaolin, mica, mica-like minerals, such as sericite type materials, magnesium carbonate, calcium carbonate, aluminum silicate, magnesium silicate, calcium silicate and clay and the like.

The most distinctive feature of the present invention is the excellent dispersibility of fine particles or ultra fine pigment or extender pigment particles (those smaller than 1 micron), such as titanium dioxide, zinc oxide, yellow iron oxides, black iron oxides, red iron oxides, ultramarine blues, Prussian blues, chromium oxides, chromium hydroxides or coal-tar pigments.

In addition to containing pigments and extender pigments as described above, molding additives may be included depending on the need, to further improve the product quality. These molding additives may be natural cellulose powder, metal soaps, calcium phosphates and like materials used in molding cosmetics or pharmaceuticals. If desired, humectants, binders and/or thickeners may also be used.

The invention is illustrated by means of preferred embodiments in the following examples.

EXAMPLE 1

The pigments or extender pigments being treated are mixed with 50 to 100% (based on the weight of pigment and extender pigment) of water and dispersed. An aqueous solution of a water-soluble compound having a lipophilic moiety, such as a water-soluble alkali metal salt of a fatty acid, is added to the slurry and dispersed. Then, 1 to 2 chemical equivalents of a water soluble salt of a polyvalent metal, such as an alkaline earth metal, aluminum, titanium, zinc or zirconium sulfate or the like is added. The polyvalent metal will then link the lipophilic moiety to the surface of the particles of pigment or extender pigment. The resultant lipophilic particles are dehydrated (but not fully dried) using a filter press and rinsed with purified water to remove any secondary salt product, if desired. It is important that the dispersion of lipophilic pigment or extender pigment particles in water not be fully dried, because in such a case an organic solvent will be necessary to form a slurry of the hydrophobic particles and the oily component, and such would be undesirable. In a preferred embodiment of the invention, the dehydration of the suspension of the lipophilic particles produces a product that contains at least about 5% water, by weight, based on the weight of the dehydrated product; more preferably, the dehydrated product contains approximately 30–60% water.

After rinsing and dehydration (but while the cake is still wet), 1 to 30% by weight of the oily component is added to the wet cake and kneaded. In this step the oily component is attached to the lipophilic moiety by displacing the surrounding water.

Water is further added, if desired, until the appropriate viscosity of the slurry is attained. Since the pigment and extender pigment particles are coated with a lipophilic moiety and surrounding oil, they are stable and form small micelles and will be in the form of an oil-in-water emulsion type slurry without the use of organic solvents or surfactants. This slurry may be injected into the rear of a pan or case using the injection machine described in U.S. Pat. No. 4,967,810 while the product is being vacuum dehydrated from the top surface via a filter. The cosmetic product is dried at an appropriate temperature. As described here, the production of cosmetic products with excellent quality are made possible with short processing time.

EXAMPLE 2

The following composition of pigments and extender pigments was mixed for one minute using a home type mixer.

| | |
|---|---|
| titanium coated mica | 40 g |
| mica | 20 g |
| talc | 40 g |
| TiO2 | 3 g |
| red iron oxide | 5 g |
| yellow iron oxide | 1 g |
| black iron oxide | 0.5 g |

The above mixture was added to 450 ml of water heated at 50° C. and mixed until well dispersed. 5 g of sodium myristate was dissolved in 50 ml of water heated at 80° C. then was added to the above mixture and mixed for 10 minutes. While this was being stirred, 1.5 chemical equivalents of aluminum chloride aqueous solution, with respect to sodium myristate, was added dropwise. This resulted in the dispersion (suspension) of the pigments surface-treated with aluminum myristate.

The resultant suspension was dehydrated by means of a centrifuge to produce a cake containing about 40% moisture. To this cake, 10 g of squalane, 0.2 g of methylparaben, and 0.2 g of butylparaben were added and kneaded. Then, 200 ml of water was added and mixed to produce the slurry for eye shadow.

Using the injection machine described in U.S. Pat. No. 20 4,967,810, this slurry was then injected into a plastic vessel from the back, as the injected material was vacuum dehydrated through its surface via a filter. Then, the product was dried at 60° C. for one hour, thereby producing a finished product.

The eye shadow obtained above had excellent skin "feel", adhesiveness, extendibility, payoff (i.e. pickup of product by an applicator), and uniformity in spite of its simple process of preparation. Moreover, the loss of cosmetic powder during the process was only 3%, thus the mess created by the powdery pigments during the process was negligible. The rate of out-of-specification product due to the non-uniformity of product surface-color and surface-hardness was zero percent.

COMPARISON EXAMPLE 1

The following composition of pigments and extender pigments was mixed for one minute using a home type mixer.

| | |
|---|---|
| titanium coated mica | 40 g |
| mica | 20 g |
| talc | 40 g |
| TiO2 | 3 g |
| red iron oxide | 5 g |
| yellow iron oxide | 1 g |
| black iron oxide | 0.5 g |

The above mixture was added to 450 ml of water heated at 50° C. and mixed until well dispersed. 5 g of sodium myristate was dissolved in 50 ml of water heated at 80° C. then was added to the above mixture and mixed for 10 minutes. While this was being stirred, 1.5 chemical equivalents of aluminum chloride aqueous solution, with respect to sodium myristate, was added dropwise. This resulted in the dispersion (suspension) of the pigments surface-treated with aluminum myristate.

The resultant suspension was dehydrated by means of a centrifuge to produce a cake containing about 40% moisture. This cake was dried at 100° C. for 12 hours and crushed by an atomizer to obtain the powder surface-treated by aluminum myristate. To this powder, 10 g of squalane, 0.2 g of methylparaben, and 0.2 g of butylparaben were added and mixed by means of a Henschel mixer and crushed by an atomizer. The resultant was screened and further mixed until uniform then charged and molded in a vessel, thereby producing a finished product.

The eye shadow obtained from above process, which took longer than the process described in EXAMPLE 2, had satisfactory quality of skin "feel", adhesiveness, extendibility, and payoff. However, the loss of cosmetic powder during the process was 25%, thus the mess created by the powdery pigments during the process was significant. The rate of out-of-specification product due to the non-uniformity of product surface-color and surface-hardness was 14%. The method was markedly inferior to that of EXAMPLE 2 in terms of workability, loss of the powder, and rate of out-of-specification product.

EXAMPLE 3

The following composition of pigments and extender pigments was mixed for one minute using a home type mixer.

| titanium coated mica | 40 g |
| sericite | 20 g |
| talc | 40 g |
| TiO2 | 3 g |
| red iron oxide | 5 g |
| yellow iron oxide | 1 g |
| black iron oxide | 0.5 g |

The above mixture was added to 500 ml of water heated at 50° C. and mixed until well dispersed. 3 g of sodium N-myristoyl-L-glutamate was dissolved in 50 ml of water heated at 80° C. then was added to the above mixture and mixed for 10 minutes. While this was being stirred, 2 chemical equivalents of zinc sulfate aqueous solution, with respect to sodium N-myristoyl-L-glutamate, was added dropwise. This resulted in the dispersion (suspension) of pigments surface-treated with zinc N-myristoyl-L-glutamate.

The resultant suspension was dehydrated by means of a centrifuge to produce a cake containing about 40% moisture. To this cake, 8 g of mineral oil, 4 g of dimethylpolysiloxane, 0.2 g of methylparaben, and 0.2 g of butylparaben were added and kneaded. Then, 150 ml of water was added and mixed to produce the slurry for eye shadow.

Using the injection machine described in U.S. Pat. No. 4,967,810, this slurry was then injected into a plastic vessel from the back, as the injected material was vacuum dehydrated through its surface via a filter. Then, the product was dried at 60° C. for one hour, thereby producing a finished product.

The eye shadow obtained above had excellent skin "feel", adhesiveness, extendibility, payoff, and uniformity in spite of its simple process of manufacture. Moreover, the loss of cosmetic powder during the process was only 3%, thus the mess created by the powdery pigments during the process was negligible. The rate of out-of-specification product due to the non-uniformity of product surface-color and surface-hardness was zero percent.

EXAMPLE 4

The following composition of pigments and extender pigments was mixed for one minute using a home type mixer.

| titanium coated mica | 10 g |
| sericite | 40 g |
| talc | 45 g |
| TiO2 | 5 g |
| red iron oxide | 1 G |
| yellow iron oxide | 2 g |
| black iron oxide | 0.2 g |
| microcrystalline cellulose | 5 g |

The above mixture was added to 400 ml of water heated at 50° C. and mixed until well dispersed. 2 g of hydrogenated egg yolk lecithin (phospholipid 30%, neutral fat 70%) was dissolved in 100 ml of water heated at 95° C. then was added to the mixture and mixed for 10 minutes. While this was being stirred, 2 chemical equivalents of aluminum sulfate aqueous solution, with respect to phospholipid, was added dropwise. This resulted in the dispersion (suspension) of pigments surface-treated with hydrogenated lecithin.

The resultant suspension was dehydrated by means of a centrifuge to produce a cake containing about 45% moisture. To this cake, 6 g of cetyl isooctanoate, 8 g of dimethyl polysiloxane, 0.2 g of methylparaben, and 0.2 g of butylparaben were added and kneaded. Then, 150 ml of the water was added and mixed to produce the slurry for powder foundation.

Using the injection machine described in U.S. Pat. No. 4,967,810, this slurry was then injected into a plastic vessel from the back, as the injected material was vacuum dehydrated through its surface via a filter. Then, the product was dried at 60° C. for one hour, thereby producing a finished product.

The powder foundation obtained above had excellent skin "feel", adhesiveness, extendibility, payoff, and uniformity in spite of its simple process of manufacture. Moreover, the loss of cosmetic powder during the process was only 2% thus the mess created by the powdery pigments during the process was negligible. The rate of out-of-specification product due to the non-uniformity of product surface-color and surface-hardness was zero percent.

COMPARISON EXAMPLE 2

The following composition of pigments and extender pigments was mixed for one minute using a home type mixer and crushed to extend the pigments by means of an atomizer to produce the powder base.

| titanium coated mica | 40 g |
| mica | 20 g |
| talc | 40 g |
| TiO2 | 3 g |
| red iron oxide | 5 g |
| yellow iron oxide | 1 g |
| black iron oxide | 0.5 g |

To this powder, 10 g of squalane, 0.2 g of methylparaben, and 0.2 g of butylparaben were added and mixed by means of a Henschel mixer and crushed by an atomizer. 300 ml of isopropyl alcohol was added to this mixture and further mixed until uniform to obtain the slurry for eye shadow.

Using the injection machine described in U.S. Pat. No. 4,967,810, this slurry was then injected into a plastic vessel from the back, as the isopropyl alcohol was vacuum vaporized from the injected material through its surface via a filter. Then, the product was dried at 60° C. for one hour, thereby producing a finished product.

The eye shadow obtained from above process had good quality in terms of payoff and uniformity of the product compared to Example 2. However, the quality of the product in terms of skin "feel", adhesiveness, and extendibility was inferior. The mess created by the powdery pigments during the process was significant especially during the first half of the process. The odor of the organic solvent was very distressing and created a concern for the work environment. The danger of flammability related to the volatile organic solvent was another concern. The loss of cosmetic powder during the process was 7%. The rate of out-of-specification product due to the non-uniformity of product surface-color and surface-hardness was zero percent.

We claim:

1. An aqueous slurry for cosmetic products, which comprises particles of pigments and/or extender pigments having a lipophilic moiety attached to the surface thereof and a cosmetically acceptable oily material dispersed in a liquid suspending medium consisting essentially of water.

2. The aqueous slurry according to claim 1, wherein the liquid suspending medium consists of water.

3. The aqueous slurry according to claim 1, wherein said particles have attached to the surface thereof a water-insoluble metal salt of a fatty acid, an acylamino acid, a hydrogenated lecithin or an acyl collagen.

4. The aqueous slurry according to claim 3, wherein said water-insoluble metal salt is a salt of a polyvalent metal.

5. The aqueous slurry according to claim 4, wherein said polyvalent metal salt is a magnesium, calcium, aluminum, titanium, zinc or zirconium salt.

6. The aqueous slurry according to claim 1, wherein said slurry consists essentially of from about 50 to about 450%, by weight, of water, and from about 1 to about 30%, by weight, of said oily component, both based on the weight of the pigment and extender pigment particles.

7. A cosmetic product formed by drying the aqueous slurry of claim 1.

8. A method of preparing the aqueous slurry of claim 1, which comprises dispersing particles of a pigment and/or extender pigment into a liquid suspending medium consisting essentially of water, adhering a lipophilic moiety to the surface of said particles while said particles are in said aqueous dispersion, and admixing a cosmetically acceptable oily component with said aqueous dispersion to form an aqueous slurry.

9. A method of preparing the aqueous slurry for cosmetic products, which consists essentially of the steps of forming a dispersion of particles of a pigment or extender pigment in a liquid suspending medium consisting essentially of water, adhering a lipophilic moiety to the surface of said particles in said aqueous dispersion, partially drying said resultant lipophilic moiety-carrying particles, admixing said partially dried lipophilic moiety-carrying particles with a cosmetically acceptable oily component to form an aqueous slurry consisting essentially of said lipophilic moiety-carrying particles and said oily component and, if desired, adding water to said slurry to adjust the viscosity thereof.

* * * * *